(12) United States Patent
Jackson

(10) Patent No.: US 6,976,960 B2
(45) Date of Patent: Dec. 20, 2005

(54) AUTOMATIC VELOCITY ANTI-ALIASED ULTRASOUND METHODS AND SYSTEMS

(75) Inventor: John I. Jackson, Menlo Park, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 183 days.

(21) Appl. No.: 10/458,156

(22) Filed: Jun. 10, 2003

(65) Prior Publication Data

US 2004/0254467 A1    Dec. 16, 2004

(51) Int. Cl.[7] ............................................. A61B 8/00
(52) U.S. Cl. ...................................... 600/437
(58) Field of Search ........................ 600/437, 438, 600/441, 442, 443, 447, 450–456; 73/861.25; 128/916; 367/7, 11, 130, 138

(56) References Cited

U.S. PATENT DOCUMENTS

| | | | |
|---|---|---|---|
| 5,363,851 A | * | 11/1994 | Hall et al. .................. 600/455 |
| 5,895,358 A | * | 4/1999 | Becker et al. ............... 600/454 |
| 6,258,029 B1 | | 7/2001 | Guracar et al. |
| 6,352,507 B1 | | 3/2002 | Torp et al. |
| 6,458,082 B1 | | 10/2002 | Jackson et al. |
| 6,464,640 B1 | | 10/2002 | Guracar et al. |
| 6,466,206 B1 | * | 10/2002 | Deering ...................... 345/419 |
| 6,475,148 B1 | | 11/2002 | Jackson et al. |
| 6,527,717 B1 | | 3/2003 | Jackson et al. |
| 6,663,566 B2 | * | 12/2003 | Pan et al. ................... 600/454 |

* cited by examiner

*Primary Examiner*—Ali Imam

(57) ABSTRACT

Velocity data is automatically anti-aliased. Since a tissue velocity varies a small amount over small distances, more accurate velocity or strain rate estimates are calculated automatically with an anti-aliasing algorithm. Since the velocity information derived from phase information, like Doppler, contains uncertainties of a multiple of a specific velocity (e.g., a constant multiple of $2\pi$ error), a specific velocity is at least one of multiple possible velocities. The possible velocities are calculated and the specific velocity selected. Additional velocities may then be extrapolated for different regions or subsequent frames of data for a same region.

23 Claims, 3 Drawing Sheets

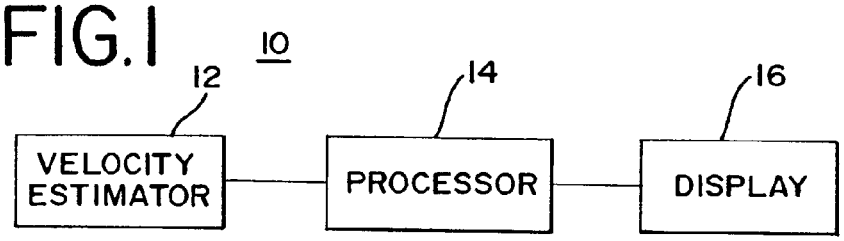
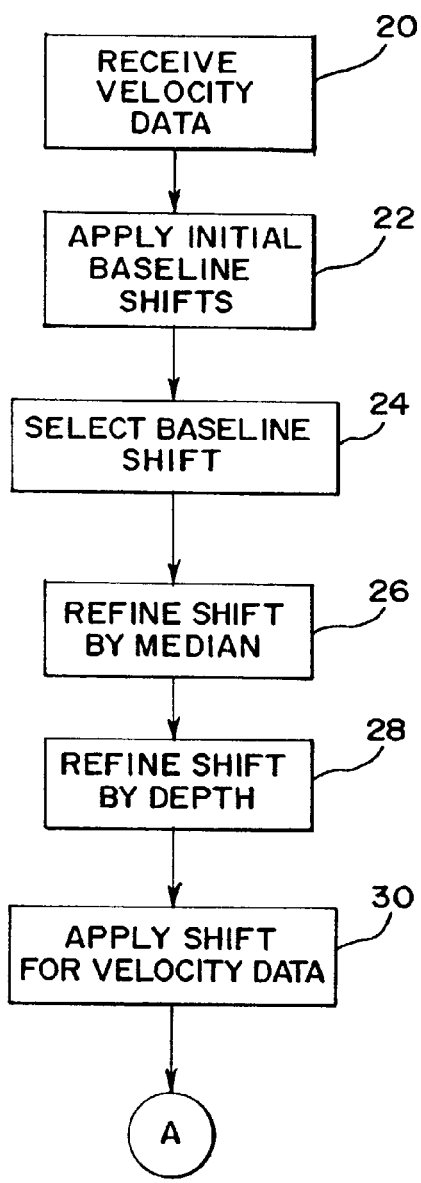
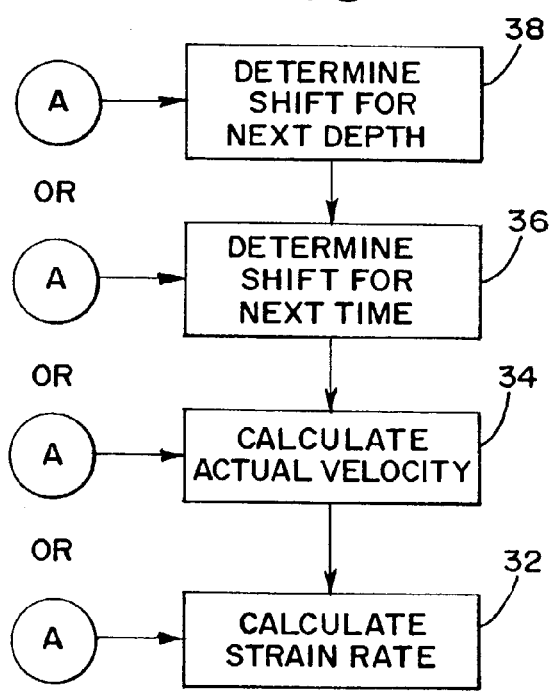

AUTOMATIC VELOCITY ANTI-ALIASED ULTRASOUND METHODS AND SYSTEMS

BACKGROUND

The present invention relates to aliasing of velocity information. In particular, anti-aliasing of phase-based ultrasound velocity estimates is automatically performed.

Ultrasound velocities are estimated within a range of velocities. The available range of velocities is dictated by the pulse repetition frequency used in pulsed transmissions of ultrasound energy to sample fluids or tissues. Velocities are estimated in response to multiple pulses. Decreasing the pulse repetition frequency (PRF) can increase the time required to generate an image of velocity information and can give under sampled, and hence erroneous velocity information. Conversely, increasing the PRF (for a fixed number of samples) will decrease the precision of velocity estimates that are not aliased, because of quantization effects. Accordingly, users typically adjust the pulse repetition frequency to be as low as possible without aliasing. Aliasing occurs where an actual velocity is beyond the Nyquist sampling range established by the pulse repetition frequency. As a result of aliasing, the velocity data is assigned an incorrect velocity value. The velocity information contains uncertainties of multiples of a specific velocity. If aliasing occurs during imaging, the physician may have to reacquire the velocity images.

Velocity imaging is used for strain rate calculations. A strain rate is calculated over one or more heart cycles, resulting in drastic differences of the maximum velocity as a function of time within the heart cycle. To avoid velocity aliasing at any point during the heart cycle, the pulse repetition frequency is set to include a maximum expected velocity within the heart cycle. The user adjusts the velocity scale and may occasionally underestimate peak velocities. A velocity scale that is too low may introduce errors into the velocity estimates because of aliasing. If aliasing does occur, an error is introduced into any strain rate calculation. Since image acquisition time is limited during a stress echo exam due to the dynamic effect of exercise or drugs during the stress cycle exam, a conservative or high velocity scale is selected by the user. The result is an unnecessarily high quantization error, which provides sub-optimal information. It has been publicly suggested that the narrow range of velocities within a short distance over tissue for a strain rate calculation should enable the strain rate to be computed even in the presence of velocity aliasing. However, no further details were provided.

BRIEF SUMMARY

The present invention is defined by the following claims, and nothing in this section should be taken as a limitation on those claims. By way of introduction, the preferred embodiments described below include methods and systems for automatic anti-aliasing of velocity data. Since a tissue velocity varies a small amount over distance, more precise velocity estimates, resulting in more accurate strain rate estimates, are calculated automatically with an algorithm even in the presence of aliasing. Since the velocity information contains uncertainties of a multiple of a specific velocity (e.g., an error corresponding to a phase error of a multiple of $2\pi$), a specific velocity is one of multiple possible velocities. The possible velocities are calculated and the specific velocity selected. Additional velocities may then be extrapolated for different regions or subsequent frames of data for a same region.

For a given PRF, a range of velocities can be accurately measured. While the span of that range is a function of the PRF, the center or baseline of the span is arbitrary. The baseline velocity can be adjusted, or shifted, from one image to another image and from one position to another position within the same image. By locally adjusting the baseline velocity shift, or baseline shift, spatial and temporal continuity assumptions can be used to un-alias velocity estimates.

In a first aspect, a method for determining velocities that exceed an aliasing velocity is provided. Velocity data that may include aliased information is received. Two or more possible sets of velocities are determined from the velocity data. For example, each possible set of velocities is calculated from a plurality of velocity scales shifted by a selected amount. One of the possible sets of velocities is then automatically selected.

In a second aspect, a method for determining unaliased velocities in the presence of velocity aliasing is provided. A first baseline velocity for a first distance range is determined. A second baseline velocity for a different second distance range is determined as a function of the first baseline velocity. Aliased velocity data associated with the second distance range is shifted in response to the second baseline velocity.

In a third aspect, a system for determining velocities that exceed an aliasing velocity is provided. A velocity estimator is operative to output velocity data that may include aliased information. A processor is operable to determine at least two possible baseline velocities from the velocity data. The first possible baseline velocity is different than the second possible baseline velocity. The processor is also operable to select one of the two possible baseline velocities.

Further aspects and advantages of the invention are discussed below in conjunction with the preferred embodiments.

BRIEF DESCRIPTION OF THE DRAWINGS

The components in the figures are not necessarily to scale, emphasis instead being placed upon illustrating the principles of the invention. Moreover, in the figures, like reference numerals designate corresponding parts throughout the different views.

FIG. 1 is a block diagram of one embodiment of a system for automatic velocity anti-aliasing;

FIG. 2 is a flowchart diagram representing one embodiment of a method of anti-aliasing;

FIG. 3 is a flowchart diagram representing another embodiment of anti-aliasing;

DETAILED DESCRIPTION OF THE DRAWINGS AND PRESENTLY PREFERRED EMBODIMENTS

Figure 4A:
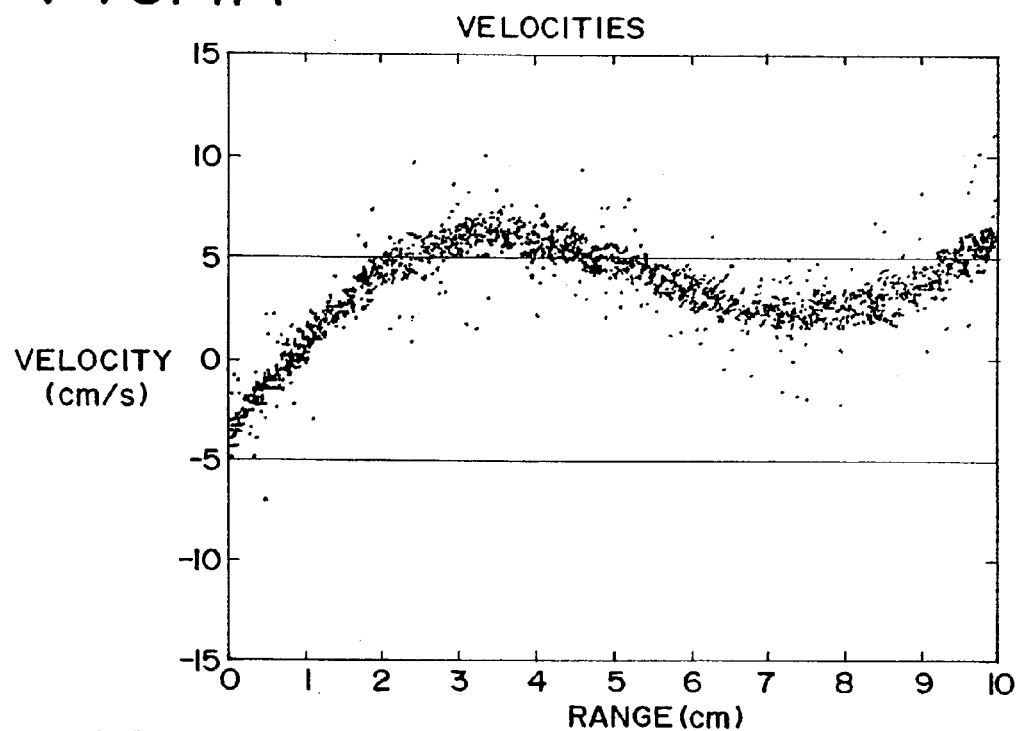
FIG. 4A is a graphical representation of one embodiment of actual velocities.

Automatic anti-aliasing is provided for the computation of the strain rate in the presence of velocity aliasing. Because the strain rate is a measure of the change in velocity as a function of distance, the strain rate is immune to a constant error in the actual velocity as long as the velocities are not differently aliased. Aliased velocities are identified by the presence of an aliasing transition, such as from a maximum positive to a maximum negative value. The same algorithm may be used to reduce the effects of aliasing and noise for calculation of actual velocities, such as where one or more initial velocities are identified as unaliased velocities.

Aliased velocities are identified by applying a plurality of baseline shifts. The shifts are each applied to the same velocity data. The baseline shift associated with the least variance of the velocity data, such as a baseline shift that centers the velocity scale around an average, median or mode velocity, is selected. The baseline shift may be further refined, such as calculating a median associated with the shifted velocities and then applying the median as the baseline shift or as an additional baseline shift. Another possible refinement is to calculate a linear regression as a function of distance of the velocity data such that a baseline shift is determined for each of multiple distances within a distance range. Using a previously calculated baseline shift for one distance range, such as the first centimeter, a baseline shift is extrapolated or estimated for velocities within a second, different distance range. In one embodiment, baseline shifts for subsequent depths are extrapolated from the linear regression or a plurality of previous baseline shifts. The linear regression is repeated in order to continue to extrapolate subsequent baseline shifts. The actual velocity or strain rate is then calculated from velocities interpreted based on the appropriate baseline shift. Since a strain rate is associated with a change in velocity, any errors due to uncertainties of possibly greater than $2\pi$ phase changes may not alter the outcome. Actual velocities may be calculated where a locally greater than $2\pi$ phase change does not exist.

The algorithm provides velocities that are unbiased by noise. Large but less than $2\pi$ changes within a range over which a single strain rate estimate is generated may be quickly calculated even in the presence of noise using the algorithm discussed above. Drastic jumps in velocity as a function of depth are unlikely, such as changes from negative to positive velocities over a short distance. By shifting velocities based on a locally estimated baseline shift, the impact of noise is minimized. Adaptive processes may be further used to identify significant noise so that different processing may be applied in different noise environments.

FIG. 1 shows a system 10 for determining velocities that exceed an aliasing velocity and/or for anti-aliasing. The system 10 includes a velocity estimator 12, a processor 14 and a display 16. Additional, different or fewer components may be provided. In one embodiment, the system 10 comprises a medical diagnostic ultrasound system. In an alternative embodiment, the system 10 comprises a computer or workstation. In yet another embodiment, the velocity estimator 12 is part of a medical diagnostic ultrasound system or magnetic resonance imaging system and the processor 14 and display 16 are part of a separate work station or remote system.

The velocity estimator 12 is a Doppler processor or cross-correlation processor for estimating velocity. An optional clutter filter may identify velocity information from a slower moving tissue as opposed to fluids or alternatively reduce the influence of data from tissue while maintaining velocity information from fluids. In alternative embodiments, another device now known or later developed for estimating velocities from any or various input data may be provided. The velocity estimator 12 receives a plurality of signals associated with a same location at different times and estimates a Doppler shift frequency, based on the average change in phase between consecutive signals from a same location. Velocity is calculated from the Doppler shift frequency. Alternatively, the Doppler shift frequency is used as a velocity. The velocity estimator 12 outputs velocity data that may include aliased information or velocities. Where an actual velocity is outside of the velocity scale or range as a function of the Nyquist sampling frequency, the velocity data is aliased. Velocity information for a particular spatial location or a plurality of spatial locations (e.g. scan lines) is output. More than one signal sample may be provided for any given spatial location. For example, 2 to 12 samples are output for each spatial location. Any of various numbers of spatial locations may be provided, such as 10 to 20 spatial locations for every centimeter over 1 to 10 centimeters of depth. Any number of samples per location as well as locations per centimeter of depth and depth ranges may be used.

Figure 4B:
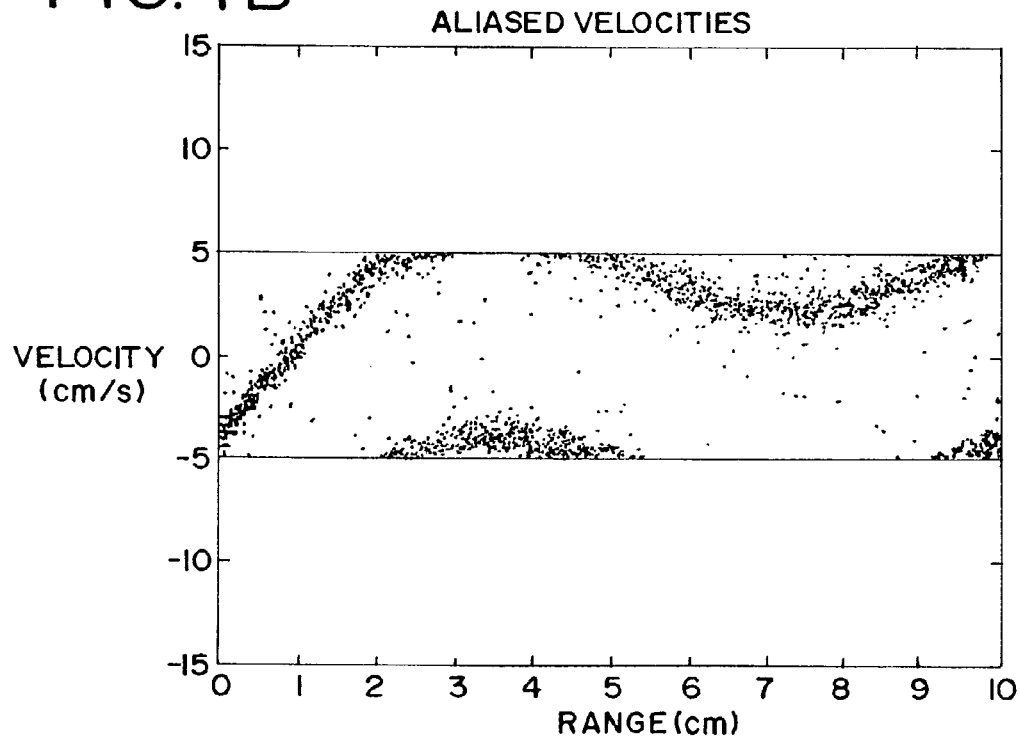
FIG. 4B is a graphical representation of the velocities including aliased velocities due to the Nyquist sampling frequency.

FIG. 4A shows a plot of velocity data as a function of range over a 10 centimeter range. The horizontal lines at 5 and −5 centimeters per second represent the Nyquist sampling frequency of the extent of the velocity scale in one example. As shown in FIG. 4B, velocities exceeding the 5 cm/s level are aliased and estimated as negative values near the −5 cm/s range. Greater or lesser aliasing may occur, and aliasing may alternatively exceed the negative velocity scale. In the examples of FIGS. 4A and 4B, the velocity samples or data represent tissue velocity information. Tissue velocities tend to change as a function of depth at a slower rate than fluid velocities. In alternative embodiments, the velocity data represents fluid velocities.

The processor 14 comprises a digital signal processor, a general processor, an application specific integrated circuit, digital circuitry, analog circuitry or combinations thereof. The processor 14 minimizes sudden changes in velocity. The processor 14 receives the velocity data from the velocity estimator 12. The processor 14 is operable to determine a plurality of possible baseline velocities or shifts from the velocity data. Each of the possible baseline velocities or shifts is different. The processor 14 is operable to select one of the plurality of possible baseline velocities or shifts for removing or anti-aliasing the velocity data where appropriate. The processor 14 identifies aliased velocity data or anti-aliases by shifting velocity data associated with a sudden change in velocity, such as shown at about 2 centimeters and 5 centimeters in FIG. 4B. By determining a baseline velocity or shift for one depth or range of depths, the processor 14 is operable to determine another baseline velocity or shift for a second range. The subsequent baseline velocity or shift is determined as a function of baseline shift or velocity determined for a different range. The identified shifts are applied to the velocity data to shift aliased velocities back to an appropriate velocity value, such as shifting velocity data from as shown in FIG. 4B to as shown in FIG. 4A.

In one embodiment, the processor 14 implements one or more of the algorithms discussed below with respect to FIGS. 2 and 3, but different algorithms may be implemented. Additional or multiple processors may be used to implement various aspects of the algorithms.

The display 16 comprises a monitor, LCD, flat panel display, printer or other display. The display 16 outputs an image responsive to anti-aliased velocity data or data calculated from anti-aliased velocity data, such as the strain rate. Alternatively, the display 16 may be connected to a data storage medium or remote workstation, from which the data can later be retrieved and displayed or printed.

FIG. 2 shows a method of one embodiment for determining and anti-aliasing velocities that exceed an aliasing velocity. Different, additional or fewer acts may be provided than shown in FIG. 2. For example, either of the refining acts 26 and 28 for the application act 30 are not provided or skipped. In one embodiment, the acts are provided as an algorithm for automatic identification and anti-aliasing. Automatic identification and anti-aliasing avoids user input and user adjustment to avoid aliasing. The processor 14 identifies aliased data and corrects the aliased data without requiring the user to reset the pulse repetition frequency.

In act 20, velocity data is received. The velocity data may include aliased information. For example, the velocity samples shown in FIG. 4A include aliased information beginning at around 2 centimeters and ending at around 5 centimeters and again around 9 centimeters. Velocity data with no aliasing or different amounts and locations for aliasing may be provided. For any given depth, the velocity range of samples is around 5 cm/s or less, but a greater or lesser range may be provided.

A baseline velocity shift, baseline value or shift in velocity (i.e. offset velocity) is determined from the velocity data. The baseline shift is a shift or correction factor applied to one or more velocity samples. In one embodiment, the baseline shift changes the values of the velocity data so that aliasing is minimized. The baseline or center portion of the velocity scale is adjusted so that the maximum number of velocity samples for a depth or range of depths is within the velocity scale after the shift. A baseline velocity for one depth sample or over a range of multiple depth samples is determined.

In act 22, a plurality of possible baseline shifts are applied to the velocity data. For example, four possible shifts are applied to velocity data representing samples from 0 to 1 centimeters as shown in FIG. 4A. A first shift is 0. The velocity data is maintained at the same values. A second shift is the velocity corresponding to an average phase change of $-\pi/2$ radians (e.g., $-2.5$ cm/s in the example of FIG. 4A). Another baseline shift is the velocity corresponding to an average phase change of $\pi/2$ radians (e.g., $+2.5$ cm/s in the example of FIG. 4A). The fourth baseline shift is the velocity corresponding to an average phase change of $\pi$ radians (e.g. 5 or $-5$ cm/s in the example of FIG. 4A). Each baseline shift is applied to all of the velocity samples or data within the selected distance range. As a result of the baseline shifts, more or less aliasing occurs. Fewer or more than four initial possible velocity offsets or baseline shifts may be used. While the shifts discussed above are uniformly spaced throughout the velocity scale, shifts with varying distribution throughout the velocity scale may be provided.

Based on the baseline shift, the range of the velocity scale is shifted, and individual velocities may require that an offset velocity (corresponding to a multiple of a phase of $2\pi$) be applied to keep the individual velocities within the modified or shifted velocity range. For example, the velocity range above is 10 cm/s. With a baseline shift of 0, the range is from $-5$ cm/s to 5 cm/s. Velocities outside of this region alias into this region and are interpreted as something else (e.g., 5.5 cm/s aliases to $-4.5$ cm/s). If a baseline shift is applied, this affects the range of velocities that are assumed to exist. A baseline shift of 1 cm/s changes the scale to range from $-4$ cm/s to $+6$ cm/s. Velocities between $-4$ cm/s and 5 cm/s are unaffected by the baseline shift. The velocities that continue to be in the shifted range are not shifted or adjusted. Sometimes a baseline shift results in a velocity being adjusted by the amount of the Nyquist velocity range. In this example, a velocity at $-4.5$ cm/s is shifted to 5.5 cm/s by a 10 cm/s shift in our example. A set of possible velocities are determined as function of the possible baseline shifts. As used herein, a set may include only one or multiple values.

In act 24, one of the possible baseline shifts or shifted sets of velocity data is automatically selected. For example, the processor 14 determines a variance of the velocity data from the velocities responsive to each of the possible baseline shifts. The standard deviation, sum of absolute differences, correlation or other measure of the spread of velocities is calculated. The baseline shift resulting in the minimal velocity variance is identified as the most likely shift associated with no aliasing. If two or more of the baseline shifts have an equal, or a nearly equal, spread of velocities, then the median of those baseline shifts is selected. The velocity data adjusted based on the selected baseline velocity is selected or maintained.

In the example shown in FIG. 4B, a $\pi$ or $+\pi/2$ radian shift results in a greater variance in the 0 to 1 cm range. A $-\pi/2$ shift may also result in greater variance. As a result, the 0 baseline shift is selected. Had the process started with the 2 to 3 centimeter range, the 0, $-\pi/2$ and $+\pi/2$ radian shifts result in more variance than a $\pi$ shift. As a result, the $\pi$ radian shift is selected.

In optional act 26, the baseline shift is refined as a function of a median velocity. The median of the velocity data adjusted by the selected baseline shift is determined. The computed median is used as a new baseline shift. The original velocity data is adjusted as a function of the median velocity. Alternatively, the velocity data adjusted by the selected initial baseline shift is further adjusted by a difference between the initial baseline and the median velocity. In alternative embodiments, a mean or mode velocity is selected for refining the baseline shift.

In optional act 28, the baseline shift is refined as a function of depth. The baseline shift is determined as a function of range, such as within the distance range used for selecting the initial baseline shift. In the example described above, the baseline shift is determined for the range of 0 to 1 centimeters or other range. Velocity data subject to the previously selected or calculated baseline shift to remove aliasing is used. The trend in the shifted velocity data as a function of range is calculated, such as determining a best fit line with linear regression or a least squares algorithm on the shifted velocity data. In alternative embodiments, low-pass filters, median filters auto regressive moving average models or other techniques are used for determining a best fit line.

The extrapolation of the best fit line to any given depth determines the baseline shift for that depth. The slope of the best fit line provides a strain rate. For example, the samples at the beginning of the 0 to 1 centimeter range are centered about $-4$, but the velocity data at the 1 centimeter location are centered at about 0. As a result, the velocity scale for 0 cm is set to $+1$ to $-9$ cm/s and the velocity scale at the 1 cm is set from 5 to $-5$ cm/s. The already shifted baseline data is further shifted by the differences between the baseline shifts for each depth and the previously applied shift. Alternatively, velocity data prior to any baseline shifting is adjusted based on the new baseline shifts determined as a function of depth. The linear regression and baseline shift process is repeated none, one or more times to refine the linear regression or calculations of baseline shift as a function of depth using previously determined shifts. As an alternative to the best fit line refinement discussed above, the initial distance or depth range used for determining the baseline shift is narrow, such as associated with velocity samples corresponding to a single depth or a few depths.

In act 30, one or more of the baseline shifts is applied to the velocity data. The application occurs as part of or after any of acts 22, 24, 26 and 28 discussed above. Where the baseline shifts have been determined as a function of depth or range of depths, the baseline shifts are applied to velocity data appropriate for a particular depth or range of depths. For example, baseline shifts determined in response to a best fit line are applied. In one embodiment, the baseline shifts determined using one of the refinements above are applied instead of the initially determined baseline shift. In alternative embodiments, a difference between a previously applied baseline shift and a subsequently determined baseline shift is calculated and velocity data responsive to a previous baseline shift is subjected to a further baseline shift based on the difference. The baseline shift is applied as discussed above (e.g. shifting the velocity range and possibly shifting any velocity values that fall outside of the shifted velocity range by the Nyquist velocity range. An average or other combination of velocity values may be alternatively shifted if outside the range due to a baseline shift. For example, an average velocity for a given depth is determined from the velocity samples and the average velocity value is adjusted by the Nyquist velocity range where the average is no longer within the baseline shifted velocity scale.

FIG. 3 shows four different possible uses of the anti-aliased velocity data. Additional or different uses may be provided. In one embodiment, the four uses are implemented together in real time, such as during a stress echo exam. In other embodiments, one or more of the uses are not used, such as calculation of actual velocities.

In act 32, the strain rate is calculated as a function of the adjusted velocity data. Regardless of the eventual baseline shift applied using the algorithm discussed above for FIG. 2, the strain rate is a function of the selected possible initial baseline shift. One or more refinements may have also been used. Even where the refined shifts replace the initially selected shift, the refinement is responsive to the initially selected shift such that the eventual strain rate is also a function of the initially selected baseline shift. Where refinements have been performed, the strain rate is also a function of the refined shifts.

The strain rate is the rate of change in velocity over a distance range, such as over the 0 to 1 centimeter distance range in the example discussed above. The rate of change in velocity is calculated by subtracting the maximum velocity from a minimum velocity within the range, by subtracting the mean, median or mode velocity at the end of the range from the corresponding velocity at the beginning of the range, by determining the slope of a straight line that best fits the velocity data within the range or other now known or later developed method for calculating strain rate. In one embodiment where linear regression or baseline shift is determined as a function of depth, the resulting best fit line or curve is used to calculate strain rate. By using shifted velocity data or anti-aliased data, the undesirable effects of a sudden change in velocity due to aliasing are avoided. As a result, a strain rate may be calculated in the presence of large noise signals. Where the actual velocities and/or noise result in largely varying velocity signals as compared to the velocity scale, the rate of change in velocity may still be appropriately identified by applying the baseline shift and corresponding shift in some velocity values as discussed above.

In act 34, an actual velocity is calculated. An error may occur where a large variance of velocity signals or noise signals as compared to the velocity scale exists. Due to the integer multiple $2\pi$ radian nature of potential error in the velocity signal, the actual velocity in the presence of aliasing may be incorrect. To avoid inaccuracies, unaliased velocity information is identified. For example, the velocity data occurring from 0 to 1 centimeter in FIG. 4b is identified as unaliased so that an actual velocity is determined. Subsequent actual velocities for different depths are then accurately determined even in the presence of aliased information based on the estimation as a function of depth discussed below for act 38. The actual velocity is determined as a function of the adjusted velocity data, such as a function of the selected possible baseline shift as described in FIG. 2 for act 24. The actual velocity may also be calculated in response to refinements or other baseline shifts with or without user input. For example, velocities at mid-diastolic or other non-aliased velocities within the cardiac cycle are identified. Using the line fitting or extrapolation discussed below for acts 36 or 38, the actual velocity is calculated even in the presence of aliasing at other parts of the cardiac cycle. The velocity from the identified time or distance is used to extrapolate velocities to subsequent or previous distances or times.

In act 38, a baseline shift is determined for a different depth range. The subsequent depth range overlaps the previous depth range but includes at least one depth that is different than the previous depth range. For example, the depth range window is moved from 0 to 1 centimeters to 0.2 centimeter to 1.2 centimeters in the example of FIG. 4B. Greater or lesser amounts of overlap may be provided, including no depth overlap. The baseline shift associated with the subsequent depth range is determined as a function of one or more of the baseline shifts determined for the first or previous depth range. For example, the subsequent baseline velocity is estimated from the first baseline velocity, such as estimated as being the same. Alternatively, the subsequent baseline is estimated to be greater or lesser than a previous baseline velocity for the previous range based on a current trend in baseline velocities over a serious of ranges. While the estimations discussed above are extrapolated from previously occurring data, interpolation or other estimation functions may be used. In alternative embodiments, the algorithm described in FIG. 2 above is repeated for each different depth range.

The baseline velocity for each subsequent depth range is a function of any of the baseline velocities calculated for different, such as a previous or subsequent, depth ranges. For example, the baseline shift for a different depth range is a function of the selected possible shift determined for a different depth range.

In one embodiment, the baseline shift for the new portion of the different range is estimated from the baseline shifts determined as a function of depth for the previous range. Any of the best fit lines or estimation techniques discussed above for act 28 may be used for determining the shift for different depth ranges. For example, by extrapolating from the linear regression, other line fitting refinements discussed above or a line determined for a strain rate calculation, an estimated base line shift for each new depth, such as at 1.1 cm and 1.2 cm in the examples discussed above for FIG. 4B, are extrapolated from the line information. The velocity scale is adjusted around the new estimated baseline shift for the new depths. Using the velocity samples, including any samples adjusted due to the baseline shift, for the new depths, the linear regression or other best fit line calculation is repeated over all previous depths, over the depths in the current depth range, such as 0.2 centimeters to 1.2 centimeters in the example discussed above over the new depths (e.g. 1.1 cm and 1.2 cm) or over another subset of depths. Using none, one, or more iterations, the estimated baseline shift for the new depths is refined. As a result of the extrapolation or estimation from previous values associated with different depths, any aliased velocity data is shifted by an appropriate amount to unalias the data.

Velocity data associated with the new depths is adjusted as a function of the estimated or calculated baseline shift. The estimation and shifting continues for subsequent or different depth ranges. As a result, aliased velocity samples are unaliased. The adjusted velocity data results in a gradual velocity transition rather than a sudden velocity transition due to aliasing. For example, the aliased velocity data shown in FIG. 4B is shifted to an appropriate position as shown in FIG. 4A. The strain rate may then be calculated for any of various distances or depth ranges.

Figure 5A:
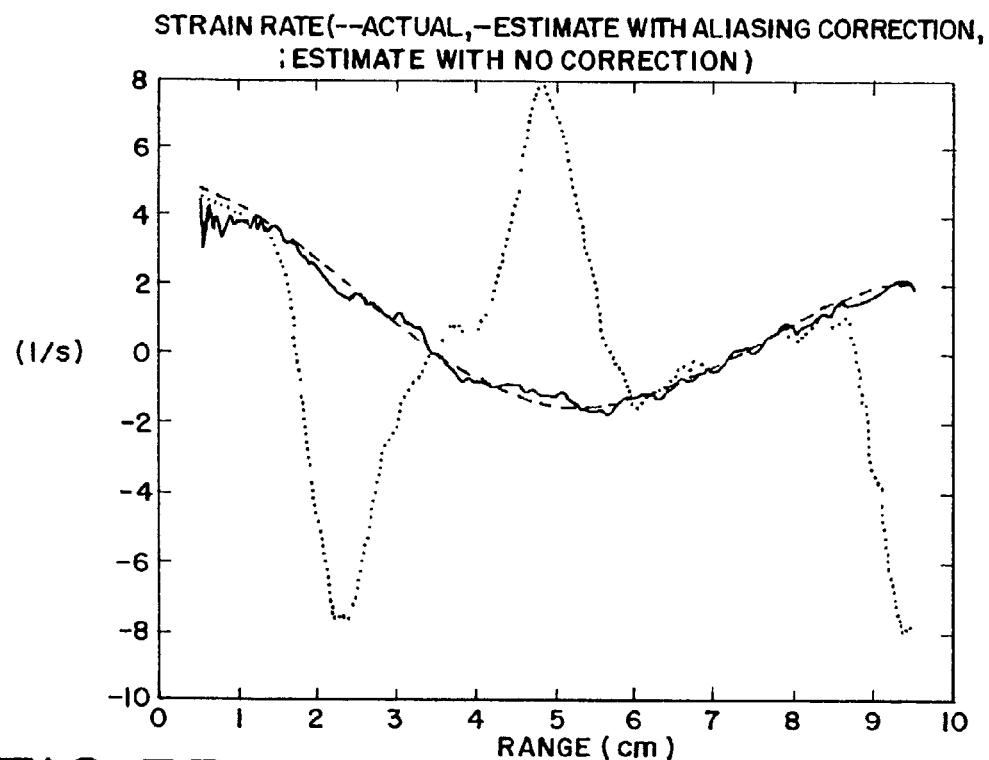
FIG. 5A is a graphical representation of embodiments of an actual strain rate, a strain rate in response to no anti-aliasing and a strain rate in response to anti-aliasing or aliasing correction.
Figure 5B:
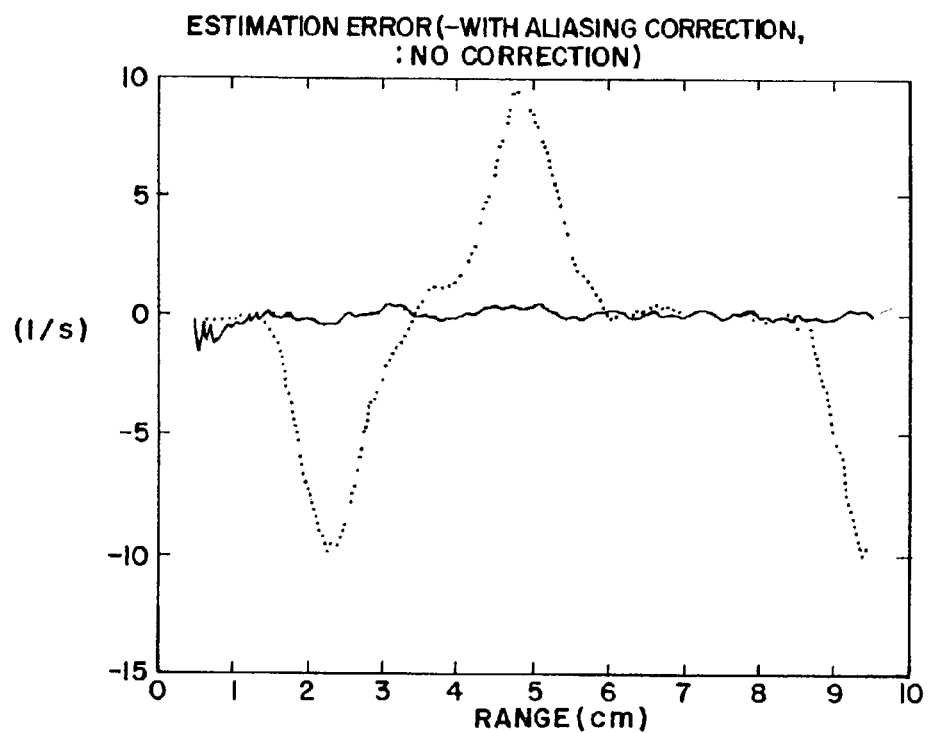
FIG. 5B is a graphical representation of the errors of the two calculated strain rates of FIG. 5A.

FIG. 5A shows the actual strain rate for the velocity data of FIG. 4A. Strain rate calculated from the velocity data provided from the estimator 12 as represented in FIG. 4B is also shown as the dotted line. Due to the velocity aliasing, sudden changes in velocity around the 2 cm, 5 cm, and 9 cm depths result in large changes in the strain rate or spikes in the strain rate. Each of the spikes represents an inaccuracy or deviation from the actual strain rate. FIG. 5A also shows a strain rate based on the anti-aliasing algorithm discussed above in FIGS. 2 and 3, including the refinement acts 26 and 28 and use of the linear regression for determining shifts for subsequent or different depths. As shown, the estimate with aliasing correction shown as the solid line is similar to the actual strain rate. As shown in FIG. 5B, the estimation error from the actual strain rate associated with the anti-aliased velocity data is very small as compared to a strain rate calculated without anti-aliasing. Since $2\pi$ phase errors are irrelevant when computing strain rate or the change in velocity, strain rate is accurately calculated.

In another embodiment, a two-dimensional image is generated from velocity values for each of a plurality of spatial locations. The velocity values are displayed in different colors as a function of different velocities. Alternatively, the velocity values are displayed in different colors as a function of a change or difference from adjacent values. The velocity values are responsive to the baseline velocity shifts discussed herein.

In act 36, the baseline shift for a subsequent frame of data acquired at a different time is determined as a function of a baseline shift from a previous frame of data. In alternative embodiments, baseline shift for a previous frame of data is determined as a function of a baseline shift determined for a subsequent frame of data, such as where the frames of data are stored. Each frame of data is associated with velocity samples acquired from a same, substantially same or overlapping region of a patient at different times, such as a difference in time sufficient to acquire velocity samples for generating a two-dimensional, spectral Doppler, one-dimensional or other image format and associated scan pattern. Since velocity data is acquired with little time between frames of data, the baseline shift may not change drastically. One or more baseline shifts for one frame of data may be used to estimate baseline shifts for another frame of data. The same shift is used or a shift is estimated from a trend in shifts for the same location as a function of time. The process is repeated using shifts from one or more frames of data for estimating a subsequent frame of data or different frame of data. Since the baseline shift for one frame of data is calculated as a function of the initial or possible baseline velocities, each subsequent baseline shift for a different frame of data is a function of the possible or initial baseline velocities. In alternative embodiments, the algorithm described in FIGS. 2 and/or 3 are repeated for each different frame of data. The baseline shift estimated for each subsequent frame of data from a baseline shift determined for a different time is responsive to the baseline shift for an immediately preceding frame of data. In alternative embodiments, baseline shifts from other than immediately preceding frame of data is used alone or in combination with other baseline shifts for estimating the current baseline shift.

Strain rate is accurately calculated even in the presence of velocity aliasing. By tracking velocity from frame to frame or depth to depth, the tissue velocities can be un-aliased to provide accurate peak velocities that exceed the aliasing velocity limit. As a result, the user may no longer be required to conservatively set the velocity scale, allowing decreased pulse repetition frequencies, reducing preparation time or work flow requirements, and reducing the potential for stress echo exams to be repeated. Accurate strain rates and velocity values are determined even in the presence of noise. The adjusted velocity data may also or alternatively be used for generating a two-dimensional tissue Doppler velocity image, two-dimensional fluid velocity image, spectral Doppler image, a strain rate graph or display of strain rate values. Other values, graphs or images responsive to anti-aliased velocity data may be used.

While the invention has been described above by reference to various embodiments, it should be understood that many changes and modifications can be made without departing from the scope of the invention. For example, velocities may be anti-aliased for velocity information representing fluids rather than tissue. As another example, a baseline shift may be characterized as a resetting or determining an actual baseline. The baseline shift may be associated with a center or other non-center portion of the velocity scale, such as positioning a baseline such that more or fewer values appear on a negative side of the scale than a positive side of the scale or vice versa. As yet another example, a greater range of values is provided on one side of a baseline than another side of the baseline.

It is therefore intended that the foregoing detailed description be regarded as illustrative rather than limiting, and that it be understood that it is the following claims, including all equivalents, that are intended to define the spirit and the scope of this invention.

I claim:

1. A method for determining velocities that exceed an aliasing velocity, the method comprising:
    (a) receiving velocity data that from a velocity estimator may include aliased information;
    (b) determining at least first and second sets of possible velocities from the velocity data, the first set of possible velocities different than the second set of possible velocities; and
    (c) automatically selecting one of the at least first and second sets of possible velocities.

2. The method of claim 1 wherein (b) comprises applying at least first and second baseline shifts to the velocity data, the first baseline shift different than the second baseline shift, and wherein (c) comprises selecting the one of the first and second sets of possible velocities with a minimal velocity variance.

3. The method of claim 1 wherein (b) comprises applying at least first and second initial baseline shifts to the velocity data, the first initial baseline shift different than the second initial baseline shift, and wherein (c) comprises selecting one of the first and second initial baseline shifts;
further comprising:
(d) determining a median velocity in response to the selected one of the first and second initial baseline shifts; and
(e) shifting the velocity data based on the median velocity.

4. The method of claim 1 wherein the velocity data represents velocity samples over a distance range, further comprising:
(d) performing a liner regression on the velocity data responsive to the selected one of the first and second sets of possible velocities; and
(e) applying a baseline shift as a function of distance within the distance range in response to the linear regression.

5. The method of claim 1 wherein (a), (b) and (c) are performed for velocity data representing velocity samples over a first distance range, further comprising:
(d) adjusting a second baseline velocity for a second distance range as a function of the selected set of possible velocities for the first distance range, the second distance range including at least one depth different than the first distance range.

6. The method of claim 4 wherein (a), (b) and (c) are performed for velocity data representing velocity samples over a first distance range, further comprising:
(d) extrapolating a second baseline velocity for a second distance range as a function of the linear regression for the first distance range, the second distance range including at least one depth different than the first distance range; and
(e) shifting aliased velocity data representing velocity samples over the second distance range based on the second baseline velocity.

7. The method of claim 1 wherein (a), (b) and (c) are performed for a first frame of data representing a region at substantially a first time, further comprising:
(d) applying a baseline value responsive to the selected one of the first and second sets of possible velocities to velocity data representing the region at substantially a second time, the second time different than the first time.

8. The method of claim 7 further comprising:
(e) repeating (d) for subsequent frames of data representing the region at different times wherein the baseline value for each frame of data is responsive to a baseline shift for a preceding frame of data.

9. The method of claim 1 further comprising:
(d) determining a strain rate as a function of the selected one of the first and second sets of possible velocities.

10. The method of claim 1 further comprising:
(d) determining an actual velocity as a function of the selected one of the first and second sets of possible velocities.

11. The method of claim 1 wherein (b) comprises determining the at least first and second sets of possible velocities from the same velocity data.

12. A method for determining unaliased velocities in the presence of velocity aliasing, the method comprising:
(a) determining a first baseline velocity for a first distance range;
(b) determining a second baseline velocity for a second distance range as a function of the first baseline velocity for the first distance range, the second distance range including at least one depth different than the first distance range; and
(c) shifting aliased velocity data for the second distance range as a function of the second baseline velocity.

13. The method of claim 12 wherein (a) comprises selecting one of a plurality of possible baseline velocities as a function of variance of velocity data from velocities responsive to the possible baseline velocities.

14. The method of claim 13 wherein (a) further comprises:
(a1) shifting the aliased velocity data by a Nyquist velocity range;
(a2) computing a median velocity of the velocity data including shifted and any unshifted velocities; and
(a3) applying a baseline shift to the velocity data as a function of the median velocity.

15. The method of claim 12 further comprising:
(d) determining baseline shifts as a function of range within the first distance range, the baseline shifts being responsive to the first baseline velocity; and
(e) applying the baseline shifts as a function of range to velocity data for the first distance range.

16. The method of claim 15 wherein (b) comprises estimating the second baseline velocity from the baseline shifts for the first distance range.

17. The method of claim 16 wherein (d) comprises performing a linear regression of the velocity data responsive ti the first baseline velocity, wherein (e) comprises applying the baseline shifts responsive to the linear regression instead of the first baseline velocity, and wherein (b) comprises extrapolating the second baseline velocity from the linear regression of (d).

18. The method of claim 12 wherein a majority of the first distance range overlaps the second distance range.

19. The method of claim 12 wherein (b) comprises extrapolating the second baseline velocity from the first baseline velocity.

20. The method of claim 12 further comprising:
(d) calculating a strain rate as a function of the shifted velocity data.

21. The method of claim 15 further comprising:
(d) calculating a strain rate as a slope of the baseline shifts.

22. A system for determining velocities that exceed an aliasing velocity, the system comprising:
a velocity estimator operative to output velocity data including aliased information;
a processor operable to determine at least first and second possible baseline velocities from the velocity data, the first possible baseline velocity different than the second possible baseline velocity, and the processor operable to select one of the at least first and second possible baseline velocities.

23. The system of claim 22 wherein the processor is operable to determine a third baseline velocity for a second distance range as a function of the selected one of the first and second possible baseline velocities, the second distance range including at least one depth different than the first distance range, and the processor operable to shift aliased velocity data for the second distance range as a function of the third baseline velocity.

* * * * *